United States Patent [19]

Chou

[11] Patent Number: 4,826,768
[45] Date of Patent: May 2, 1989

[54] POLYOXYALKYLENE GLYCOL CONVERSION TO MONOCARBOXYLIC ACID

[75] Inventor: Kechia J. Chou, Wappingers Falls, N.Y.

[73] Assignee: Texaco Inc., White Plains, N.Y.

[21] Appl. No.: 43,015

[22] Filed: Apr. 27, 1987

[51] Int. Cl.$^4$ ................................................. C12P 7/42
[52] U.S. Cl. ..................................... 435/146; 435/822
[58] Field of Search ................................ 435/146, 822

[56] References Cited

FOREIGN PATENT DOCUMENTS 0021593  2/1981  Japan .................................... 435/146
0085296  5/1984  Japan .................................... 435/146

OTHER PUBLICATIONS

Derwent Abs. 86-207845/32 Nakano Su Ten (J61139387) 6-86.
Derwent Abs. 85-279150/45 Nakano Su Ten (J60188069) 5-85.
Derwent Abs. 85-052896/09 Beppu (J60009488) 1-85.
Derwent Abs. 88-175975/26 Babel et al. (DD-253836) 2-88.
Derwent Abs. 86-220742/34 Sansho Seiyaku (J61143314) 7-86.
Derwent Abs. 80-76068C/43 Sagami Chem (J55118438) 9-80.
Derwent Abs. 78-69974A/39 Nippon Oils (J78031233) 9-78.
Derwent Abs. 79-78164B/43 Agency (J54119089) 9-79.
Derwent Abs. 77-75202Y/42 Ajinomoto KK J52108088 (9-77).
Derwent Abs. 76-46946X/25 Kanegafuchi J51051573 (5-76).
Japio 87-296883 Suzuki J62296883 (12-87).
Biotech. 83-03325 Grant et al. Biotech Bioeng (1983) 25,2,627-30.

*Primary Examiner*—Herbert J. Lilling
*Attorney, Agent, or Firm*—Robert A. Kulason; James J. O'Loughlin; Robert B. Burns

[57] ABSTRACT

A method for converting a polyoxyalkylene glycol to the corresponding monoacid which comprises forming a mixture of a polyoxyalkylene glycol, a Gluconobacter species and a nutrient medium is provided.

9 Claims, No Drawings

POLYOXYALKYLENE GLYCOL CONVERSION TO MONOCARBOXYLIC ACID

This invention relates to a process for converting a polyoxyalkylene glycol to a monocarboxylic acid. More specifically, this process involves a microbial conversion, process wherein a polyoxyalkylene glycol having a molecular weight ranging from about 150 to 5000 is converted to its corresponding monocarboxylic acid.

BACKGROUND OF THE INVENTION

Polyoxyalkylene glycols represent a useful class of compounds because they have a wide range of product applications as well as having utility as components or reactants in the synthesis of a variety of complex compounds. The polyoxyalkylene glycols compounds are widely available commercially. The usefulness of this class of compounds could be substantially enlarged by the incorporation of another functional group in the basic compound. The new compounds would possess new physical properties as well as a broader range of chemical applications.

DISCLOSURE STATEMENT

A variety of strains of acetic acid bacteria have been employed to effect the oxidation of alkanediols. Acetobacter aceti and Gluconobacter oxydans have been disclosed as effective for oxidizing certain alkane glycols to the corresponding monocarboxylic acid. For example, 1,2-ethanediol has been oxidized to glycolic acid and 1,3-propanediol has been oxidized to beta-hydroxypropionic acid using species of these microorganisms. The glycol, 1,4-butanediol has been oxidized to succinic acid and 1,5-pentanediol has been oxidized to glutaric acid. The nature of the starting substrate appears to be a major factor in determining the type of oxidized product produced in a conversion process employing the noted microorganisms.

Many experiments have been conducted attempting to effect the oxidation of glycols with microorganisms and many have met with variable results. It has been reported that Acetobacter aceti, Acetobacter xylinum and Gluconobacter suboxydans did not oxidize 1,2-butanediol, 1,2-pentanediol or 1,2-hexanediol. Little is known on the effectiveness of the acetic acid bacteria for oxidizing polyoxyalkylene glycols particularly those having higher molecular weights. "THE OXIDATION OF GLYCOLS BY ACETIC ACID BACTERIA" by K. Kersters and J. DeLey published in Biochim. Biophys. Acta 71 31191963 summarizes many experiments on the bacterial oxidation of glycols.

BRIEF DESCRIPTION OF THE INVENTION

A method has now been discovered for converting higher polyoxyalkylene glycols having molecular weights ranging from 150 to 5000 or above to the corresponding monoacid which comprises contacting the polyxyalkylene glycol with a Gluconobacter species in a nutrient medium, comprising a yeast extract, peptone and a carbohydrate selected from the group consisting of mannitol and glucose, under aerobic conditions together with control of the pH of the reaction mixture to produce a monocarboxylic acid corresponding to the starting polyoxyalkylene glycol.

DETAILED DESCRIPTION OF THE INVENTION

According to this invention, a polyoxyalkylene glycol such as triethylene glycol and polyoxyalkylene glycols having over 150 molecular weight is converted to its corresponding monocarboxylic acid by contacting the polyoxyalkylene glycol with a Gluconobacter species in a nutrient medium comprising a yeast extract, peptone and a carbohydrate selected from the class consisting of mannitol and glucose, under aerobic reaction conditions at a temperature ranging from about 5° to 50° C. with the hereinafter described control of the pH of the reaction mixture to effect a substantially complete conversion of the polyoxyalkylene glycol substrate to the corresponding monocarboxylic acid. The temperature for the reaction, the aerobic reaction conditions, and control of the pH of the reaction mixture, as well as the nature of the nutrient mixture are all essential to the effectiveness of this process.

Examples of polyoxyalkylene glycols which may be employed in the conversion process of the invention include triethylene glycol, tetraethylene glycol, pentaethylene glycol and polyoxyethylene glycols having molecular weights ranging from 150 to about 5000 molecular weight or above. The polyoxyalkylene glycol reactant may be represented by the following structural formula:

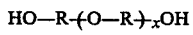

wherein R is a divalent alkylene radical having from 2 to 3 carbon atoms and x has a value from 1 to 100 or above.

The polyoxyalkylene glycol is converted to the corresponding monocarboxylic acid by bacterial action, namely by the action of a Gluconobacter species under the prescribed conditions. Specific Gluconobacter species effective in the instant process include *Gluconobacter roseus* IAM 1841 and *Gluconobacter oxydans* ATCC 621. Other suitable Gluconobacter species include oxydans ATCC 14960.

The composition of the nutrient medium is considered to be critical in order to effectively convert the polyoxyalkylene glycol to the corresponding carboxylic acid. The nutrient medium employed in this reaction comprises as essential components a yeast extract, peptone and a carbohydrate selected from the class consisting of mannitol and glucose. Mannitol is the preferred carbohydrate. Essentially no loss in efficiency was found when the carbohydrate consisted of a mixture of mannitol and glucose. In general, the nutrient medium comprises the following amounts of the essential components, from about 0.25 to 1 weight percent of the yeast extract, from about 0.1 to 0.75 weight percent peptone and from about 1 to 5 weight percent of the carbohydrate. A typical nutrient medium will contain about 0.5 wt. % of yeast extract, about 0.3 wt. % of peptone and about 2.5 wt. % of mannitol. This process is conducted under aerobic conditions that is in the presence of air or in an oxygen-containing (aerobic) gas or atmosphere. The general method of operating is to pass a stream of air or the aerobic gas or medium through the nutrient medium containing the polyoxyalkylene glycol and the Gluconobacter species. A preferred way of introducing the air or aerobic gas is to bubble a stream of same through the reaction medium. The rate of such gas bubbling through the reaction medium is not considered to be critical. However, it has been found advantageous to bubble air or an aerobic equivalent through the reaction medium at a rate of about 500 to 1000 ml of air per minute per liter of the reaction mixture comprising the nutrient medium, polyoxyalkylene glycol substrate and the Gluconobacter species.

It is essential to maintain a suitable reaction temperature in the reactor. In general, the reaction is conducted at a temperature ranging from about 5° to 50° C. It is preferred to effect the reaction at a temperature from about 25° to 35° C.

A critical feature in conducting this reaction is the control of the pH of the reaction mixture. At the start of the reaction, the nutrient medium is essentially neutral, that is, the nutrient medium will have a pH of about 7.0. As the reaction progresses and the polyoxyalkylene glycol is gradually converted to the corresponding monocarboxylic acid, the acidity of the nutrient medium increases. This is reflected in a lowering of the pH of the reaction mixture comprising the nutrient medium, the polyoxyalkylene glycol, the Gluconobacter species and the newly formed monocarboxylic acid product. The acidity of the nutrient medium reaction mixture will increase as reflected by a drop of the pH of the reaction mixture to a pH of about 4.0 or below. When the reaction mixture has become acidified to the point where it has a pH of 4 or 3.9, it is essential that the pH of the reaction mixture be readjusted to a substantially neutral condition, that is to a pH of about 7. This is vital in order to promote substantially complete conversion of the polyoxyalkylene glycol substrate to its corresponding monocarboxylic acid. Any base that will not interfere with the proper functioning of the components in the reaction mixture can be employed for effecting this neutralization. Examples of suitable bases include sodium hydroxide, potassium hydroxide et al. In general, sodium hydroxide is the preferred material for this purpose.

The product of the reaction, namely the monocarboxylic acid corresponding to the polyoxyalkylene glycol substrate may be represented by the formula:

HO—R—(O—R—)$_x$COOH where R and x have the values noted above.

The following examples represent the practice of this invention:

EXAMPLE I

Preparation of the monoacid from triethylene glycol

A 10% innoculum of *Gluconobacter roseus* and 40 g(2% by weight) of triethylene glycol were placed in a fermenter with 2 liters of a nutrient medium containing yeast extract 0.5%, peptone 0.3% and mannitol 2.5%. The fermenter was controlled at 30° C. with a constant rate of air bubbling at 750 ml/min. The culture was allowed to grow for one day under these conditions. After 24 hours, the pH of the reaction mixture was 3.5. This was adjusted to 7 by the addition of sodium hydroxide. This speeded up the reaction and the triethyleneglycol was completely converted to the corresponding monoacid in the second 24 hours. No other side product was observed in HPLC. The grown cells were removed by centrifugation. The broth was concentrated, followed by liquid-liquid extraction with dichloromethane. The dichloromethane solution was concentrated to give 42 grams of monoacid, a 96% yield.

EXAMPLE II

Large scale preparation of the monoacid from triethylene glycol

A 10% innoculum of *Gluconobacter roseus* and 800 g (8%) of triethylene glycol were placed in a 10 liter fermenter. The reaction conditions followed were the same as those employed in example I. At the end of the 48 hours, the triethylene glycol was completely converted to the corresponding monoacid.

EXAMPLE III

Preparation of monoacid from PEG 200

In a 2 liter fermenter,

A 10% innoculum of *Gluconobacter roseus*, 20 g(1%) of PEG 200 and a nutrient medium as described in Example I were placed in a 2 liter fermenter. The reaction was conducted as in Example I. After 2 days, the starting material was completely converted to the corresponding monoacid.

EXAMPLE IV

Preparation of monoacid from PEG 400

100 ml of a nutrient medium as described in Example I were placed in a 250 ml flask. A loopful of Gluconobacter ATCC 621 and 2 mmol of PEG 400 were added. The reaction was controlled at 30° C. in a shaker bath for 2 days. The cells were removed. Analysis found that 50% of the PEG 400 had been converted to the corresponding monoacid.

Examples I to III above demonstrate that the novel process of the invention is effective to convert substantially all of a polyoxyalkylene substrate to the corresponding acid. The reaction will not go to completion and mixtures of monoacid and diacid will be formed if the pH of the reaction mixture is not returned to neutral after it has dropped to a pH of about 4. Example IV is illustrative of an incomplete reaction.

EXAMPLE V

*Gluconobacter roseus* IAM 1841 was grown with 1% triethylene glycol in the medium described above in a shaker flask controlled at 30° C. The pH was not controlled at all. The initial pH was 6.3. After two days the pH dropped to 3.0. Only 60% of the starting material, triethylene glycol, was utilized. The consumption of triethylene glycol was increased to 72% when the reaction was allowed for two more days. The pH remained at 3.0. The products contained a mixture of monoacid, diacid and trace amounts of unknown materials.

I claim:

1. A method for converting a polyoxyalkylene glycol to the corresponding monoacid which comprises forming a mixture of a polyoxyalkylene glycol, a Gluconobacter species and a nutrient medium in a fermenter, said glycol having a molecular weight from about 150 to 5000 and said nutrient medium comprising a neutral mixture of a yeast extract, peptone and a carbohydrate selected from the group consisting of mannitol and glucose, reacting said mixture under aerobic conditions at a temperature ranging from about 5° to 50° C. to initiate said conversion resulting in the lowering of the pH of said reaction mixture to a pH of about 4 or below, raising the pH of said reaction mixture to a pH of about 7 and continuing said reaction until said polyoxyalkylene glycol has been completely converted to said monoacid.

2. A method according to claim 1 in which said Gluconobacter species is selected from the group consisting of *Gluconobacter roseus* and *Gluconobacter oxydan* (ATCC 621).

3. A method according to claim 1 in which said carbohydrate is mannitol.

4. A method according to claim 1 in which said aerobic reaction is conducted by bubbling air through said mixture at a rate of from about 500 to 1000 ml of air per minute per liter of said mixture.

5. A method according to claim 4 in which air is bubbled through said mixture at a rate of 600 to 800 ml of air per minute per liter of said mixture.

6. A method according to claim 1 in which said Gluconobacter species is *Gluconobacter roseus*.

7. A method according to claim 1 in which said glycol is triethylene glycol.

8. A method according to claim 1 in which said glycol is a polyoxyalkylene glycol having a molecular weight from about 200 to 1000.

9. A method according to claim 1 in which said reaction is conducted at a temperature ranging from about 25° to 35° C.

* * * * *